United States Patent
Shah et al.

(10) Patent No.: US 10,149,980 B2
(45) Date of Patent: Dec. 11, 2018

(54) SYSTEM AND METHOD FOR IMPLANTABLE ELECTRICAL CONNECTOR

(71) Applicant: Lawrence Livermore National Security, LLC, Livermore, CA (US)

(72) Inventors: Kedar G. Shah, San Francisco, CA (US); Satinderpall S. Pannu, Pleasanton, CA (US); Susant Patra, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 28 days.

(21) Appl. No.: 14/748,782

(22) Filed: Jun. 24, 2015

(65) Prior Publication Data

US 2016/0380381 A1    Dec. 29, 2016

(51) Int. Cl.
*H01R 12/77* (2011.01)
*H01R 12/78* (2011.01)
*A61N 1/375* (2006.01)
*H01R 13/24* (2006.01)
*H01R 13/621* (2006.01)

(52) U.S. Cl.
CPC ....... *A61N 1/3752* (2013.01); *H01R 13/2421* (2013.01); *H01R 13/621* (2013.01)

(58) Field of Classification Search
CPC ...... H01R 12/716; H01R 12/77; H01R 12/78; H01R 13/5208; H01R 13/5219; H01R 2201/12; H01R 13/5224
USPC ..... 607/115, 116, 53, 54; 439/909, 289, 271
See application file for complete search history.

(56) References Cited

U.S. PATENT DOCUMENTS

| 4,116,517 A | * | 9/1978 | Selvin | H05K 3/365 29/846 |
| 4,255,003 A | * | 3/1981 | Berg | H01H 1/24 333/247 |
| 4,516,820 A | * | 5/1985 | Kuzma | A61N 1/3754 439/271 |
| RE33,170 E | * | 2/1990 | Byers | A61F 2/18 128/903 |
| 5,782,645 A | * | 7/1998 | Stobie | A61N 1/02 439/289 |
| 5,832,601 A | * | 11/1998 | Eldridge | B23K 20/004 257/620 |

(Continued)

*Primary Examiner* — Michael A Lyons
*Assistant Examiner* — Matthew T Dzierzynski
(74) *Attorney, Agent, or Firm* — Harness, Dickey & Pierce LP (57) ABSTRACT

A high density electrical connector system is disclosed which may make use of first and second connector components. The first connector component has a first substrate with a first plurality of electrical feedthroughs and at least a first plurality of electrically conductive bond pads in communication with the first plurality of electrical feedthroughs. The second connector component has a second substrate with a second plurality of electrical feedthroughs and at least a second plurality of electrically conductive bond pads in communication with the second plurality of electrical feedthroughs. An electrical coupling subsystem is disposed between the first and second connector components and makes electrical contact between associated pairs of the first and second pluralities of electrically conductive bond pads. A plurality of fasteners may be used for clamping the first and second connector components in facing relationship.

13 Claims, 12 Drawing Sheets

(56) References Cited

U.S. PATENT DOCUMENTS

| | | | | |
|---|---|---|---|---|
| 6,551,112 B1* | 4/2003 | Li | G01R 1/0466 | |
| | | | 439/66 | |
| 7,534,127 B2* | 5/2009 | Parker | A61N 1/36032 | |
| | | | 439/425 | |
| 7,731,517 B2* | 6/2010 | Lee | H01R 12/592 | |
| | | | 439/271 | |
| 8,000,804 B1* | 8/2011 | Wessendorf | A61N 1/0543 | |
| | | | 607/115 | |
| 8,529,277 B2* | 9/2013 | Williams | H01R 12/716 | |
| | | | 439/369 | |
| 2014/0350652 A1* | 11/2014 | Suwito | A61N 1/0541 | |
| | | | 607/116 | |
| 2015/0157862 A1* | 6/2015 | Greenberg | A61B 5/6868 | |
| | | | 607/60 | |
| 2015/0382118 A1* | 12/2015 | Vaishya | A61N 1/36032 | |
| | | | 607/57 | |

* cited by examiner

SYSTEM AND METHOD FOR IMPLANTABLE ELECTRICAL CONNECTOR

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to electrical connector systems, and more particularly to an implantable electrical connector system especially well suited for making a reversible, high density electrical connection between two electrical components.

BACKGROUND

The statements in this section merely provide background information related to the present disclosure and may not constitute prior art.

Currently, there are a limited number of methods for making sealed, implantable electrical connections. The most commonly used system in neurostimulator devices is the BalSeal SYGNUS® implantable contact system available from Bal Seal Engineering, Inc., or similar solutions. With the BalSeal SYGNUS® implantable contact system, a cylindrical male connector consists of metal contacts along the circumference of the connector. The female connector consists of a series of coiled metal rings that form a diameter smaller than the male connector, separated by silicone as a barrier for moisture. The female connector is typically assembled onto a hermetically-sealed electronics package with electrical feedthroughs, and interconnected using laser welded metal wires. The male connector also contains molded silicone features that enable a physical seal between the female connector inlet and the cylindrical male connector. While this solution is satisfactory for present day cardiac and neuro-stimulation applications with 2-16 channels, it is significantly limited in electrical connection density. Presently available connectors require a male connector of diameter around 1 mm, with a contact density of ~5 connections per 10 mm. The female connector is even larger in diameter and length than the male connector.

For the next generation of neural interface devices, there is a growing need for a significantly higher number of channels. Current neuro-stimulation devices typically have 2-16 channels, where a standard connector may be acceptable. However, for new devices with hundreds or even thousands or more of independent channels, it is no longer feasible to use bulky electrical connectors. Applications in the neural space which are being investigated at the present time will require literally hundreds of independent channels requiring hundreds of independent connections.

SUMMARY

In one aspect the present disclosure relates to a high density electrical connector system having a first connector component and a second connector component. The first connector component may have a first substrate. The first substrate may have a first plurality of electrical feedthroughs and at least a first plurality of electrically conductive bond pads in communication with the first plurality of electrical feedthroughs. The second connector component may have a second substrate. The second substrate may have a second plurality of electrical feedthroughs and at least a second plurality of electrically conductive bond pads in communication with the second plurality of electrical feedthroughs. An electrical coupling subsystem may be disposed between the first and second connector components to make electrical contact between associated pairs of ones of the first plurality of electrically conductive bond pads and ones of the second plurality of electrically conductive bond pads. A plurality of fasteners may be used for clamping the first and second connector components in facing relationship such that the first and second pluralities of electrically conductive bond pads are in electrical contact with one another through the electrical coupling subsystem.

In another aspect the present disclosure relates to a high density electrical connector system. The system may comprise a housing with at least one access port formed in the housing. A first connector component may be secured in the access port. The first connector component may have a first substrate, with the first substrate having a plurality of electrical feedthroughs and at least a first plurality of electrically conductive bond pads in communication with the first plurality of electrical feedthroughs. A second connector component may be incorporated which has a second substrate, with the second substrate having dimensions enabling it to be inserted into the first access port. The second substrate of the second connector component may further include an electrical coupling subsystem. The second connector component may be insertable into the access port such that the electrical coupling subsystem makes a plurality of independent electrical connections with the first plurality of bond pads, to thus form a plurality of independent electrical paths between the electrical coupling subsystem and the plurality of electrical feedthroughs.

In still another aspect the present disclosure relates to a method of forming a high density electrical connector system. The method may comprise forming a first connector component having a first substrate; forming a first plurality of electrical feedthroughs in the first substrate; and forming a first plurality of electrically conductive bond pads on a surface of the first substrate, which are each in communication with respective ones of the first plurality of electrical feedthroughs. The method may also comprise forming a second connector component having a second substrate; forming a second plurality of electrical feedthroughs in the second substrate; and forming at least a second plurality of electrically conductive bond pads on the second substrate, which are each in communication with respective ones of the second plurality of electrical feedthroughs. The method may further comprise placing an electrical coupling subsystem between the first and second connector components to make electrical contact between associated pairs of ones of the first plurality of electrically conductive bond pads and ones of the second plurality of electrically conductive bond pads. The method may further comprise using a plurality of fasteners for clamping the first and second connector components in facing relationship such that the first and second pluralities of electrically conductive bond pads are electrically coupled to one another through the electrical coupling subsystem.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
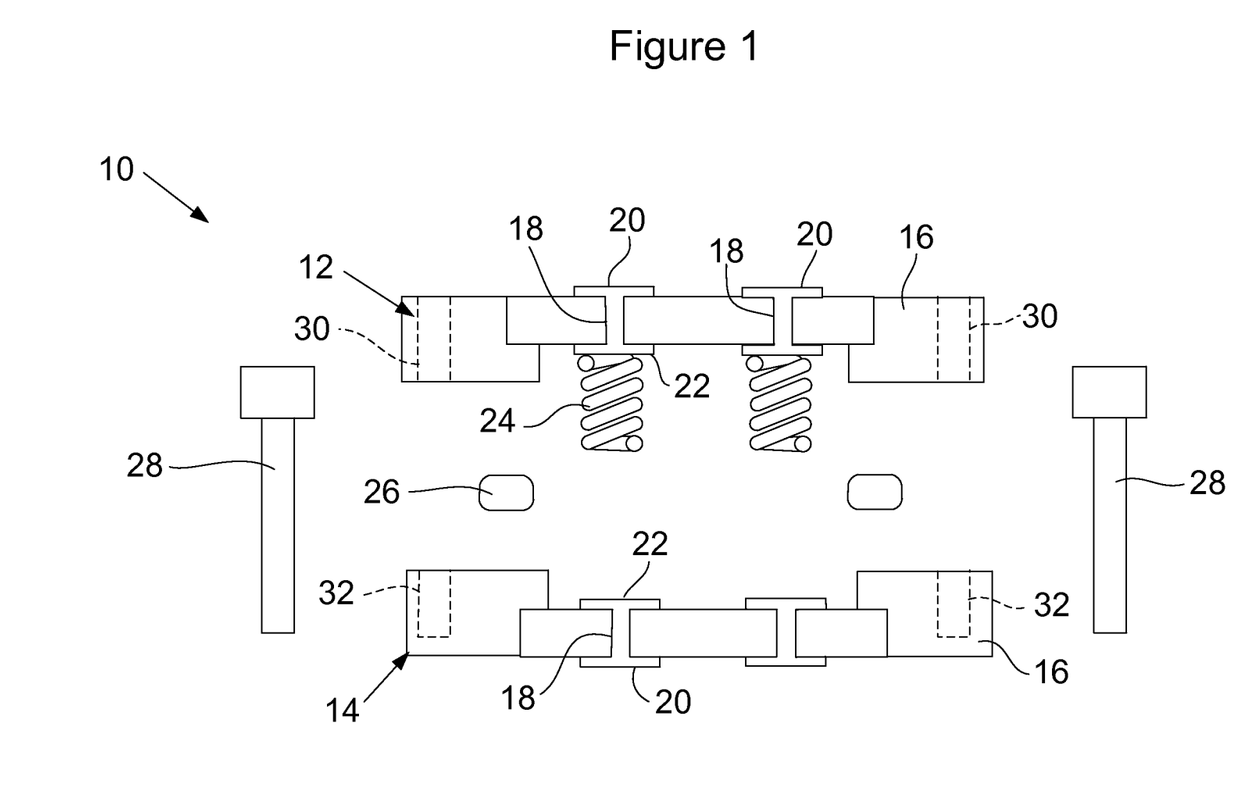
FIG. 1 is a high level schematic drawing of a connector system in accordance with one embodiment of the present disclosure that incorporates a pair of substrates with electrical feedthroughs and a plurality of electrically conductive biasing elements that enable electrical connections to be made between electrical feedthroughs on each substrate.

Referring to FIG. 1 there is shown one embodiment of a connector system 10 in accordance with the present disclosure for making a large plurality of electrical connections within a relatively small area. The connector system 10 may include first and second connector components 12 and 14. In this example connector component 12 includes a substrate 16 to which a plurality of electrical feedthroughs 18 are attached. Electrical feedthroughs 18 may have a first plurality of independent conductive bond pads 20 exposed on one side of the substrate 16, and a second plurality of independent electrically conductive bond pads 22 exposed on the opposite side of the substrate. Each electrical feedthrough 18 essentially forms an electrically conductive via that is electrically coupled to one of the bond pads 20 and one of the bond pads 22. The connector component 14 is constructed in the same fashion to likewise include components 16, 18, 20 and 22. Alternatively, the electrical feedthroughs 18, however, do not necessarily need to be vertical so as to extend through to opposing surfaces of a substrate. Put differently, the electrical feedthroughs 18 could be formed similar to traces on a printed circuit board to consist of multiple layers of conductors and insulators that are "routed" form different layouts on the top and bottom of an associated substrate.

The first connector component 12 in FIG. 1 also includes a plurality of independent, electrically conductive biasing elements 24. The biasing elements 24 collectively form an electrical coupling subsystem. In one embodiment the electrically conductive biasing elements 24 may form miniature coil springs. The biasing elements 24 may be formed from any suitable electrically conductive material although materials such as Nitinol (Ti—Ni alloy), MP35N alloy, Platinum (Pt), Platinum Iridium (Pt—Ir), Niobium (Nb) or any other bio-compatible metal/alloy. While the biasing elements 24 are illustrated as coil springs in this example, they need not necessarily take the shape of coil springs. It is possible that shapes such as, without limitation, leaf springs could be implemented as well. Each of the biasing elements 24 is each electrically coupled to an associated one of the bond pads 22, to thus form a complete conductive path through the biasing element, through its associated bond pad 22, through its associated electrical feedthrough 18 and through its associated bond pad 20.

Figure 2:
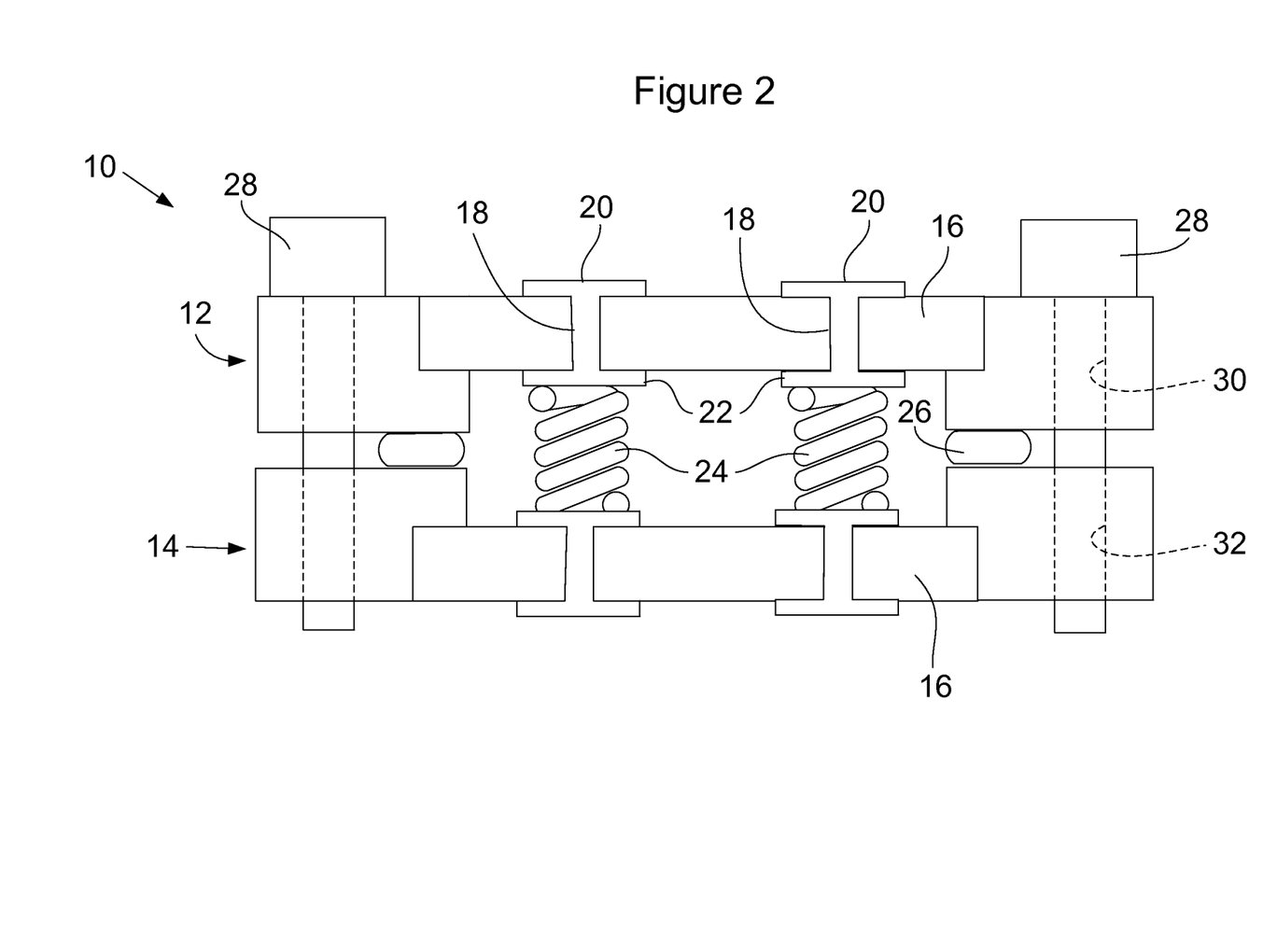
FIG. 2 is a view of the connector system of FIG. 1 but with the two substrates coupled together via a plurality of fastening elements.

Optionally, but preferably, an electrical isolation and sealing ring 26 may be included to circumscribe, and therefore seal, the biasing elements 24 and bond pads 22 from an ambient atmosphere. The sealing ring 26 may be constructed from silicone or any other suitable, electrically non-conductive, bio-compatible material with a degree of compressibility. Suitable fastening elements, in one example threaded screws 28, may be inserted through holes 30 in the connector component 12 and into blind threaded holes 32 in the connector component 14 to clamp the two connector components together with the sealing ring 26 sandwiched between them. In lieu of threaded fastening screws, mechanical clamps could also be used to clamp the two connector components 12 and 14 together. The assembled system 10 is shown in FIG. 2.

The electrically conductive components 18, 20, 22 and 24 are preferably fabricated from bio-compatible materials. Advantageously, the electrically conductive biasing elements 24 are configured in an array of connection points, as opposed to only a linear configuration of connections. This system 10 enables a modular approach to configuring electrical connectors which enhances the ease with which a large plurality of electrical connections can be made between virtually any combination of electronic chips, micro-fabricated electrode array, traditional electrical leads, electronic packages and electrical feedthroughs.

The substrates 16 may comprise ceramic or any other suitable material. The substrates 16 may be formed using LTCC or HTCC (low-temperature or high temperature co-fired ceramic technology), or extruded via an extrusion process, or possibly formed using electrodeposition techniques. The substrates 16 may each be bonded or otherwise attached to separate multi-conductor electrical cables (not shown) using laser welding, resistance welding, thermocompression bonding or any other suitable method of attachment. The electrically conductive biasing elements 24 may be attached to the bond pads 22 using solder, ultrasonic bonding, thermocompression bonding, brazing, laser welding or possibly even electrically conductive adhesives.

Creation of the electrical feedthroughs 18 and the bond pads 20 and 22 may be by thin-film (PVD) or thick-film (e.g., stencil printing or electroplating). The thin-film or thick-film may also contain a diffusion barrier for high-temperature processing. The sealing ring 26 may be attached to one of the substrates 16 using a brazing process. The sealing ring 26 itself may be fabricated by laser cutting or micromolding of silicone, or may form a conventional O-ring seal made of a biocompatible material. One suitable material for the sealing ring 26 is silicone. One or more alignment features may be incorporated into the substrates 16 and/or the sealing ring 26 itself to help align the sealing ring 26 on the two substrates in a highly precise manner during assembly of the system 10.

Figure 2A:
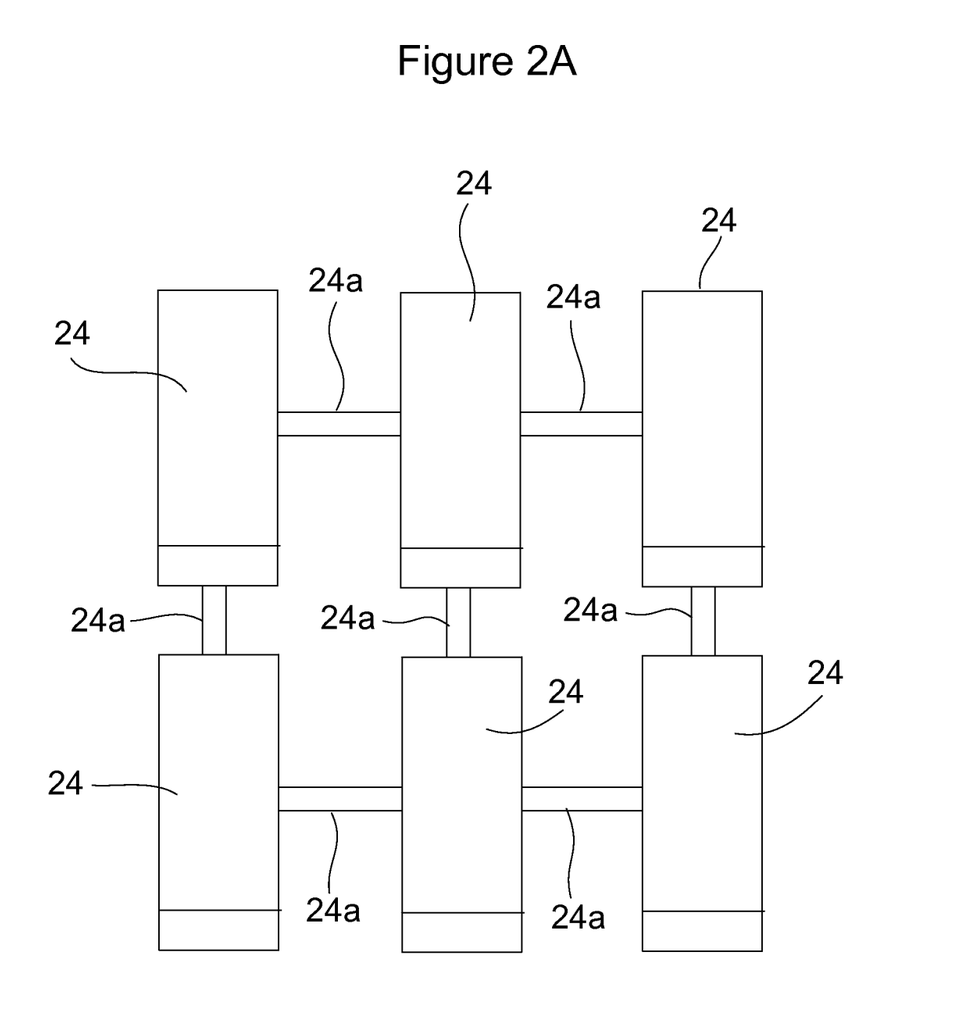
FIG. 2A is a plan view of a single cluster of electrically conductive biasing elements held in a predetermined configuration by sacrificial material portions, where the sacrificial material portions are intended to be removed in a subsequent manufacturing operation after all of the biasing elements of the single cluster have been secured to their respective bond pads.

Still further, the electrically conductive biasing elements 24 could be formed in a cluster or group of biasing elements and held in a specific configuration by sacrificial portions of material. This is shown in FIG. 2A, where the biasing elements 24 are interconnected by sacrificial material portions 24a. The sacrificial material portions 24a comprise the same material used to form the biasing elements 24 (e.g., in one example metal). The sacrificial material portions 24a serve to hold the electrically conductive biasing elements 24 in a highly precise configuration during an attachment process while the biasing elements 24 are attached to a selected plurality of the bond pads 22. Thereafter, the sacrificial metal links could be fully or partially removed by dicing or laser trimming. This process is expected to significantly reduce manufacturing time for the system 10. Alternatively, or in addition to using the sacrificial material portions 24a, the electrically conductive biasing elements 24 may be formed with a custom molded silicone insert completely or substantially surrounding each biasing element 24 to provide an additional degree of electrical isolation.

As indicated in phantom in FIG. 1, one (or both) of the substrates 16 may have mounted on it one or more electronic components or subsystems such as, without limitation, a processor, memory, amplifier, multiplexer, application specific integrated circuit (ASIC), etc. The electronic component or subsystem may be in communication with the bond pads 20. Alternatively, the bond pads 20 may be in communication with planar circuit traces formed on or within the substrate 16 and may lead out to an edge portion of the substrate where an electrical connection may be made with an independent circuit board or with an independent cable.

Figure 3:
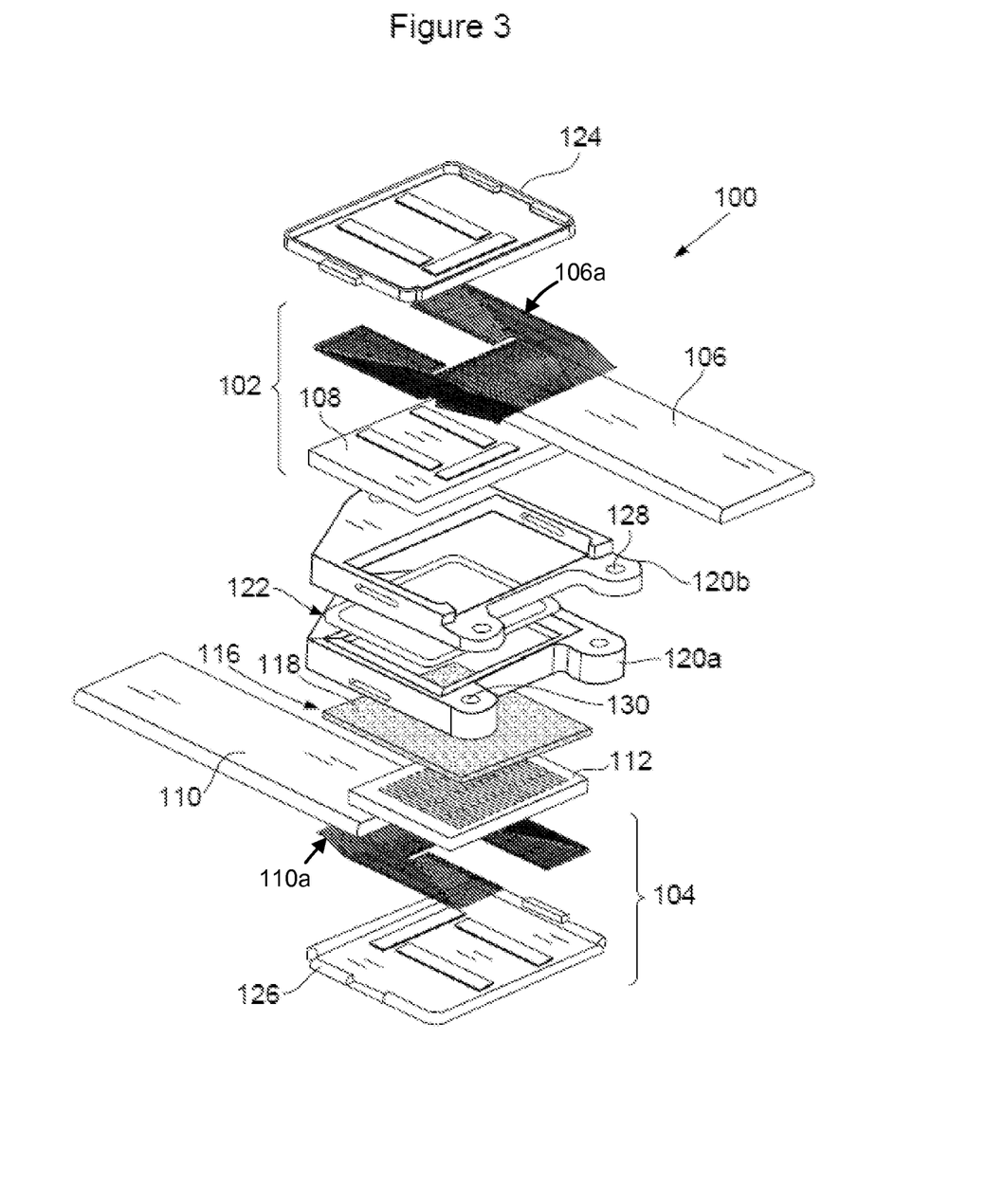
FIG. 3 is a view of connector system in accordance with another embodiment of the present disclosure which makes use of an electrically conductive interconnect sheet which is positioned between two connector components to form a plurality of independent electrical connections between the bond pads of the two connector components.
Figure 3A:
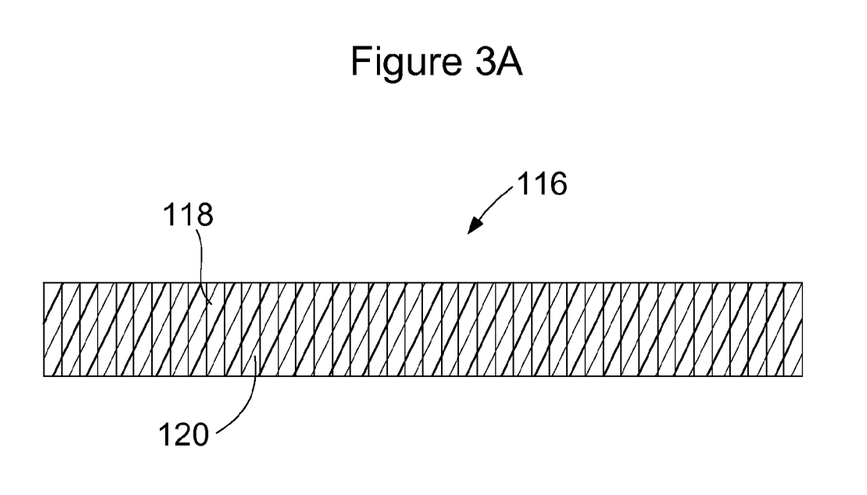
FIG. 3A is a simplified side cross sectional view of the interconnect sheet shown in FIG. 3 illustrating a plurality of densely packed wires embedded in an electrically non-conductive substrate material in a vertical orientation.

FIGS. 3 and 3A illustrate a system 100 in accordance with another embodiment of the present disclosure. With specific reference to FIG. 3, the system 100 makes use of a first electrical connector component 102 and a second electrical connector component 104. First electrical connector component 102 makes use of a multi-conductor electrical cable 106 with conductive wires 106a and a substrate 108 (e.g., ceramic substrate). Likewise, second electrical connector component 104 includes a multi-conductor electrical cable 110 with conductive wires 110a and a substrate 112 (e.g., ceramic substrate). The individual conductors at the ends of the electrical cables 106 and 110 are attached or otherwise formed in their respective substrate 108 or 112 to form electrical feedthroughs. Electrical bond pads 114 may be formed by thin film or thick film metal contacts (FIG. 4) on each of the substrates 108 and 112. The bond pads 114 may be formed in a configuration which enables electrical contact to be made with the conductors of its respective electrical cable 106 or 110 in a densely packed limited area, which would be difficult or impossible to achieve with previously used electrical connector systems.

With further reference to FIG. 3, the system 100 differs from the system 10 through the use of an independent, electrically conductive interconnect sheet 116 that serves to make the plurality of independent electrical connections between the bond pads 114 on each of the substrates 108 and 112. The interconnect sheet 116 is shown in FIG. 3A in simplified cross section and includes a large plurality of independent linear lengths of electrically conductive wires 118 embedded in a generally planar, non-conductive, biocompatible material 120, for example silicone, which has a small degree of resiliency and/or compressibility. Optionally, microsprings or conductive particles could be embedded in the biocompatible material 120. The wires 118 may typically be on the order of 0.0005 inch-0.005 inch (0.0127 mm-0.127 mm) in diameter and are exposed at each of their terminal ends. The density of the wires 118 is greater than the density of the bond pads 114. For example, in a given area which includes four independent bond pads 114, the number of independent wires 118 present within the corresponding area of the interconnect sheet 116 may be 4-100 times the number of bond pads present. In this manner, a relatively large subplurality of the wires 118 make contact with each of the bond pads 114 on both of the substrates 108 and 112, but those wires 118 that are not positioned directly between a corresponding pair of bond pads 114 make no contact with any other portions of the substrates 108,112, and therefore have no effect on operation of the system 100. In this manner alignment of the interconnect sheet 116 is not critical to forming connections between corresponding pairs of the bond pads 114.

Figure 3B:
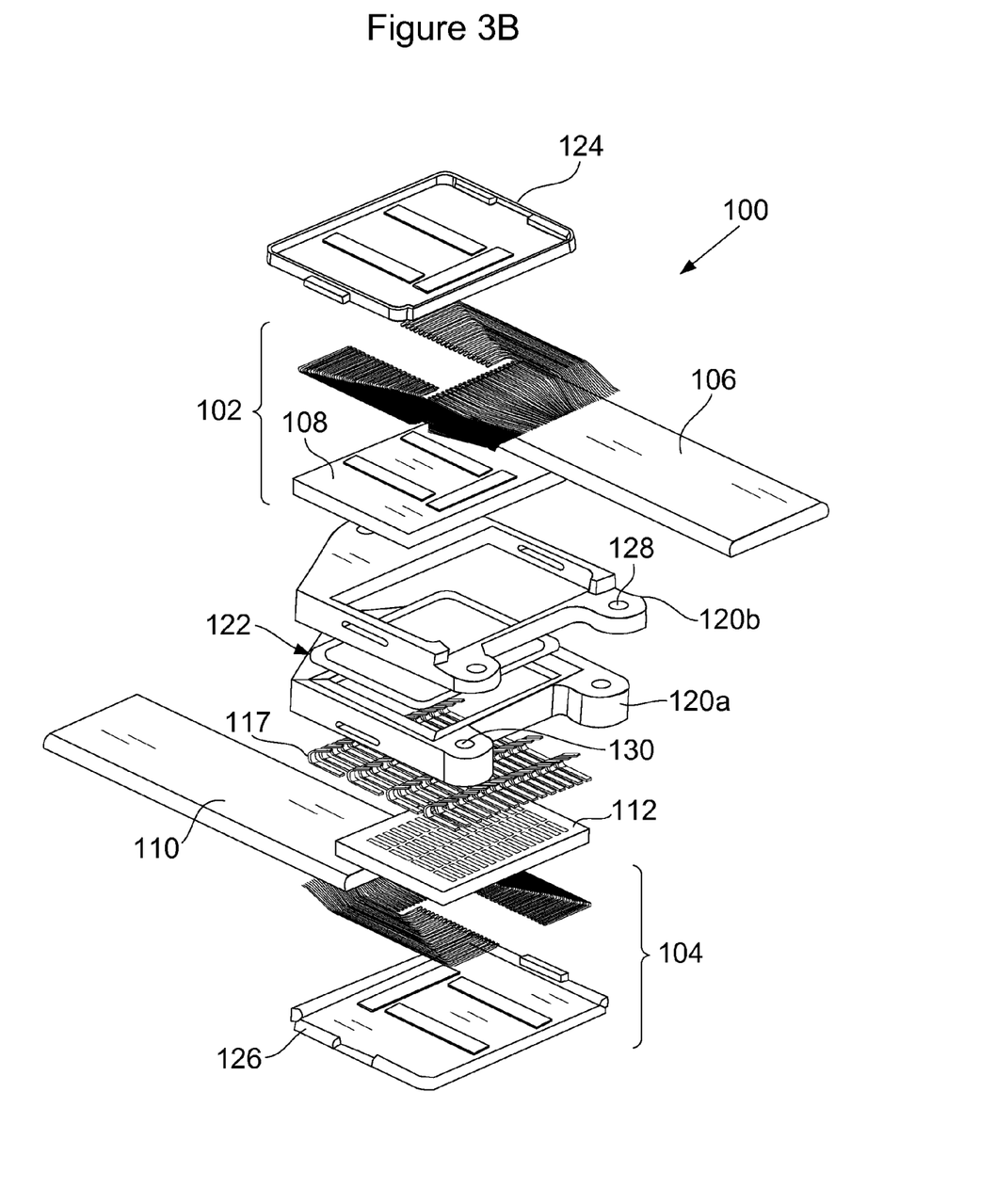
FIG. 3B is a perspective view of another embodiment of the connector system which is substantially similar to the embodiment of FIG. 3, but rather uses independent electrically conductive biasing elements instead of the interconnect sheet of the embodiment of FIG. 3.
Figure 4:
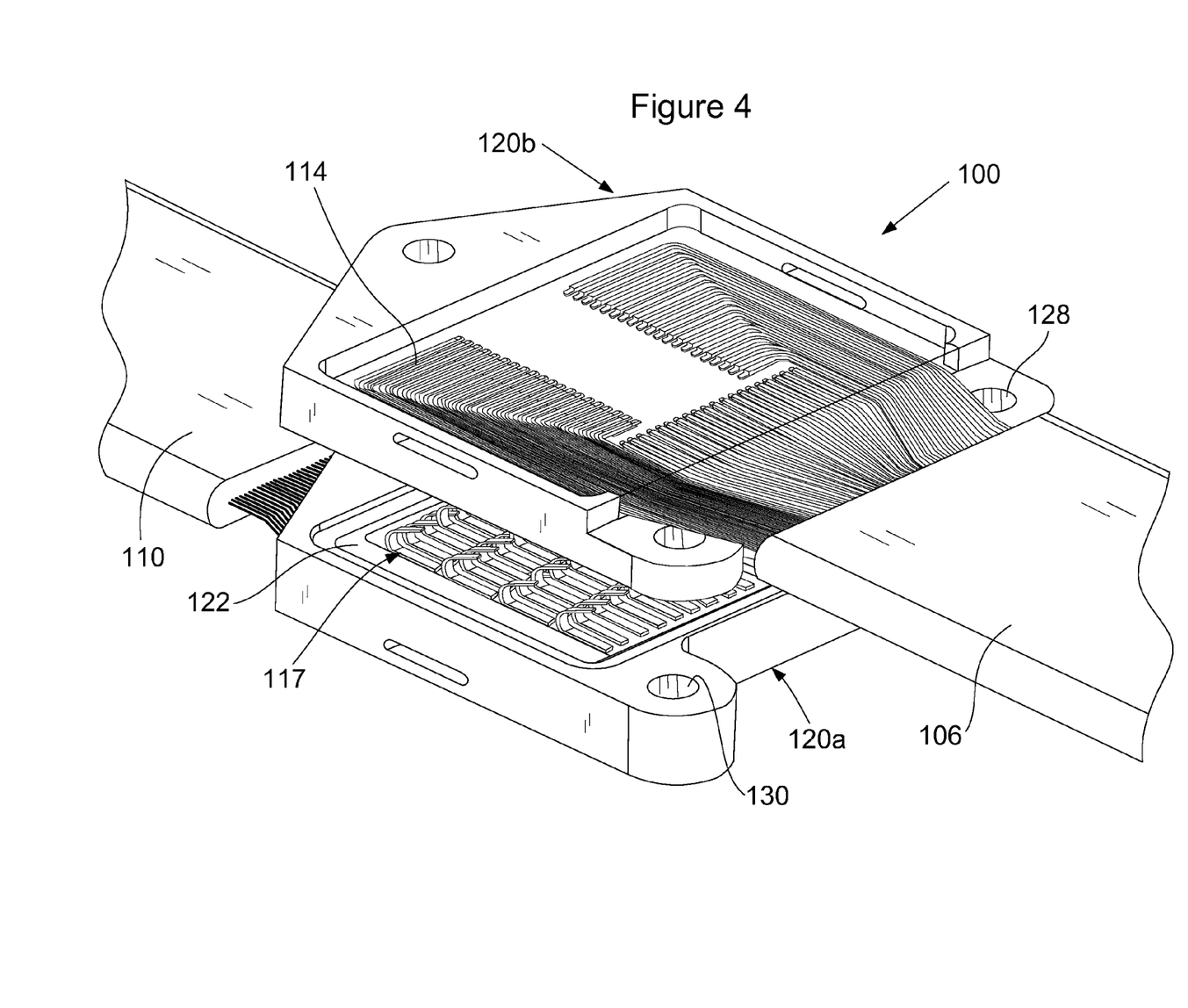
FIG. 4 is a perspective view of the connector components of the connector system of FIG. 3B about to be secured to one another with the electrical coupling subsystem positioned therebetween.
Figure 5:
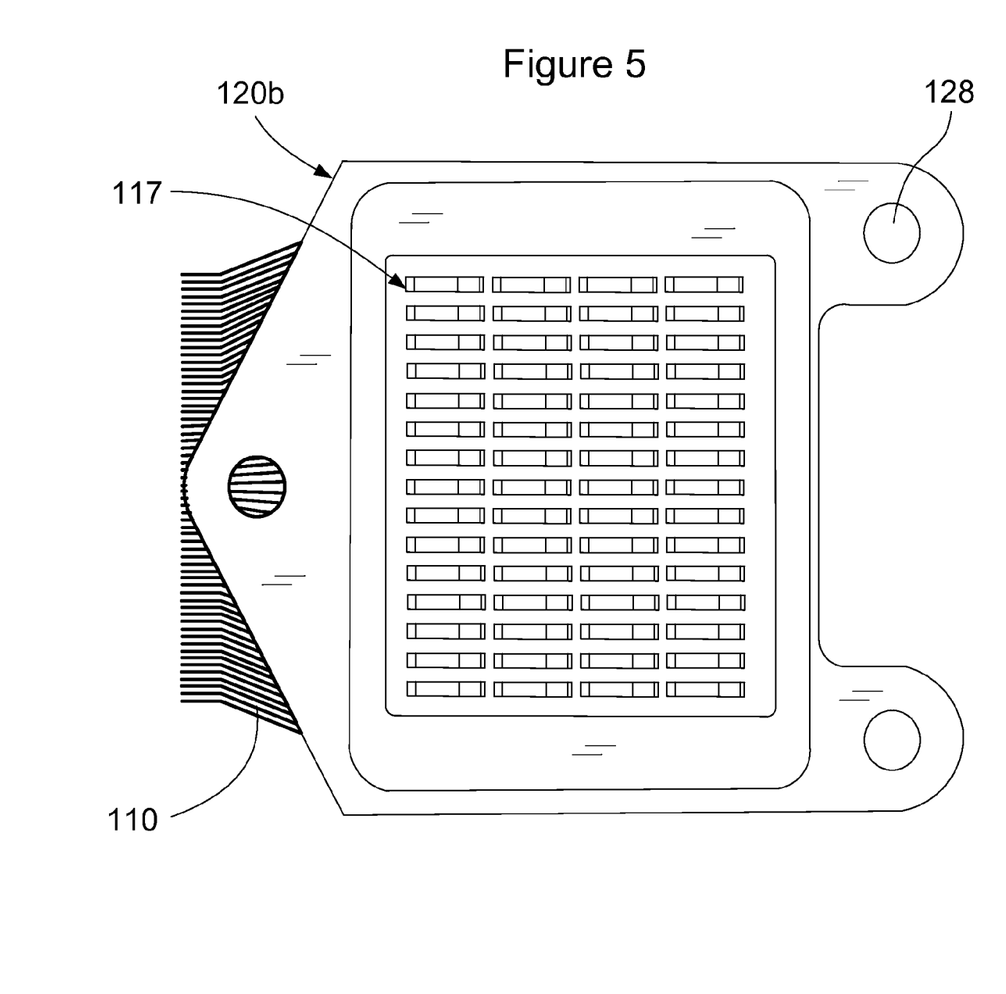
FIG. 5 is a plan view of the electrical coupling subsystem shown in FIG. 3B positioned over one of the connector components.
Figure 6:
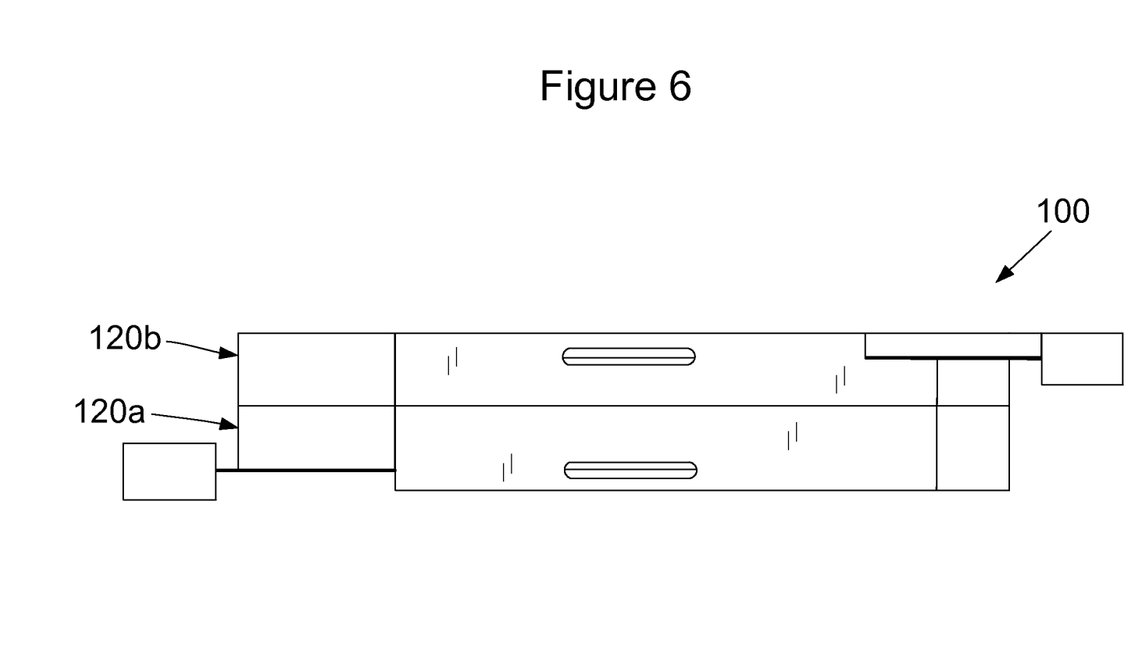
FIG. 6 is a side view of the two connector components of FIG. 4 positioned against one another.

With further reference to FIG. 3, a housing formed by mating components 120a and 120b may be used to receive the substrates 108 and 112, as well as a gasket 122. The gasket 122 may be made from silicone or any other biocompatible, electrically non-conductive material that has at least a small degree of compressibility enabling it to form a seal which circumscribes the interconnect sheet 116 and the substrates 108 and 112. Cover members 124 and 126 each having resilient latches or tabs may be connected to portions of the one or the other of the housing components 120a or 120b to cover the substrates 108 and 112. Threaded screws (not shown in FIG. 3) may also be inserted through holes 128 in housing portion 120a and into threaded bores 130 in housing portion 120b to secure the gasket 122 and the interconnect sheet 116 in place. Another embodiment of the connector system 100 of FIG. 3 is shown in FIG. 3B, with the only modification being the use of electrically conductive microsprings 117 in place of the interconnect sheet 116. FIGS. 4-6 show the connector system 100 being assembled with the microsprings 117, although it will be appreciated that the assembly of the system 100, if it incorporated the interconnect sheet 116, would otherwise be the same. Also microsprings could be formed so as to be substantially enclosed, but having portions exposed at upper and lower surfaces thereof, in an electrically non-conductive material, for example silicone. It will be appreciated that the microsprings 117, while shown for clarity in the exploded perspective view of FIG. 3B without being attached to any other component, will typically be secured to one substrate, such as substrate 112, by bonding. The bonding may be performed during a preliminary manufacturing step. With either the interconnect sheet 116, or the microsprings 117 substantially enclosed in silicone, an integrated ambient seal could also be formed around the periphery of the assembly, for example using the silicone, while seals the electrically conductive wires 118 or the electrically conductive microsprings 117 from the ambient environment.

Each of the ceramic substrates 108 and 112 with its array of feedthroughs may be bonded to its respective electrical cable using laser welding, resistance welding, thermocompression bonding, or any other method. The bond sites are preferably encapsulated in silicone or epoxy for electrical isolation. Either one, or both, of the cables 106 and 110 may be coiled or molded for modifying mechanical properties.

Each one of the substrates 108 and 112, with its array of feedthroughs, may form the hermetic feedthroughs separating the high-density connector system 100 from the implantable electronics. In this scenario, one of the feedthrough substrates may be brazed into a hermetic metal package housing an electronics subsystem.

Instead of a ceramic substrate with feedthroughs and vertical interconnects provided by the interconnect sheet 116, a multi-layer ceramic structure may be used that converts the area array of contacts into a linear array of contacts that exit an edge of the ceramic substrate. This arrangement may simplify bonding of a cable to the ceramic substrate, or for integrating electronics internal to a package within the housing components 120a and 120b of the system 100. Still further, a microelectrode array, such as a polymer flexible substrate, may be electrically bonded to the outside of the ceramic feedthrough array using a process such as rivet bonding, conductive epoxy attachment or similar.

Figure 7:
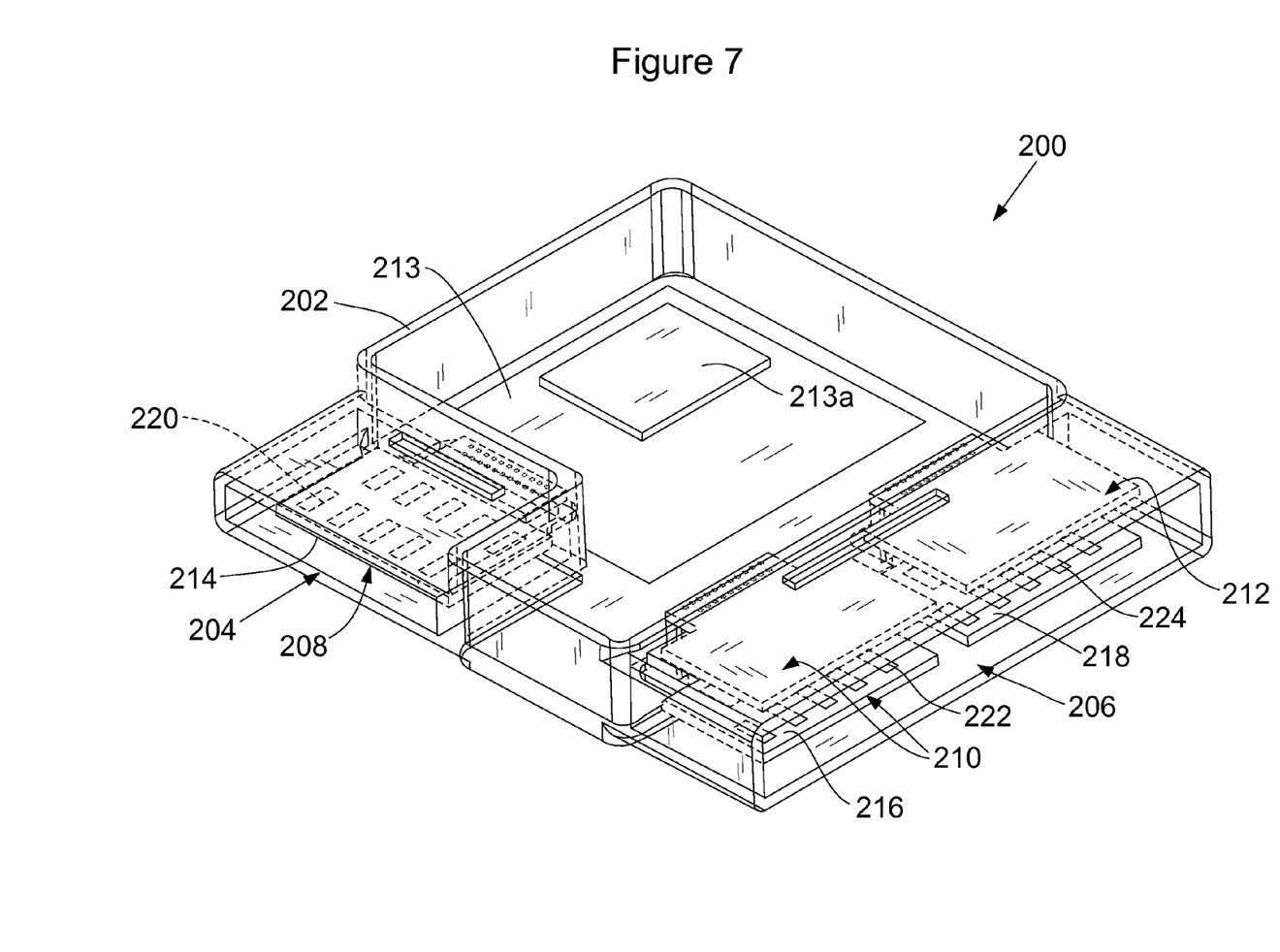
FIG. 7 is a perspective view of a connector assembly in accordance with another embodiment of the present disclosure, wherein the connector assembly makes use of a housing having a plurality of connection interfaces which each form access ports in which connector components may be located to permit sliding insertion of a male connector component.

Referring to FIG. 7 there is shown a connector system 200 in accordance with another embodiment of the present disclosure. The system 200 in this example makes use of a housing 202 having a plurality of connection interfaces 204 and 206, which form access ports to the housing 202, and where electrical connections can be made to independent electrical cables or even other independent circuit boards. The housing 202 may consist of a hermetically sealed package or enclosure with planar electrical connector components 208, 210 and 212. In this example a pair of opposing connector components 210 and a pair of opposing connector components 212 are positioned in the connection interface 206. In this example, using pairs of connector components 210 and 212 enables double the number of independent electrical connections to be made at the connection interface 206. The connector components 208-212 may be in communication with a circuit board 213 having one or more electrical subsystems 213a thereon. Alternatively, the circuit board 213 and one or more of the connector components may be formed as a single integrated assembly. The connector components 208-212 need not be the same dimensions or have the same electrical connection capacities, although in the example of FIG. 7 they are shown as being identical. Likewise, while the housing 202 is shown having a substantially square shape, the housing could have virtually any shape to best meet the needs of an intended application. Whatever dimensions/capacities are chosen for the connector components 208-210, the dimensions of the connection interfaces 204 and 206 will need to be sized to accommodate the connector components being positioned therein. The connector components 208-212 may be secured to the housing 202 by, for example, brazing, laser welding, thermocompression bonding, or any other suitable means of attachment. It is possible that separate connectors such as threaded screws and/or clamping structures could also be used to secure the two connector components 208-210 within the housing 202. The connector components 208-210 may have substrates 214, 216 and 218 formed from a ceramic material, (e.g., AL203 or polyimide) with bond pads 220-224 formed thereon. The bond pads 220-224 are in electrical contact with electric feedthroughs, not visible in FIG. 7, but similar or identical in construction to electrical feedthroughs 18 shown in FIG. 1.

Figure 8:
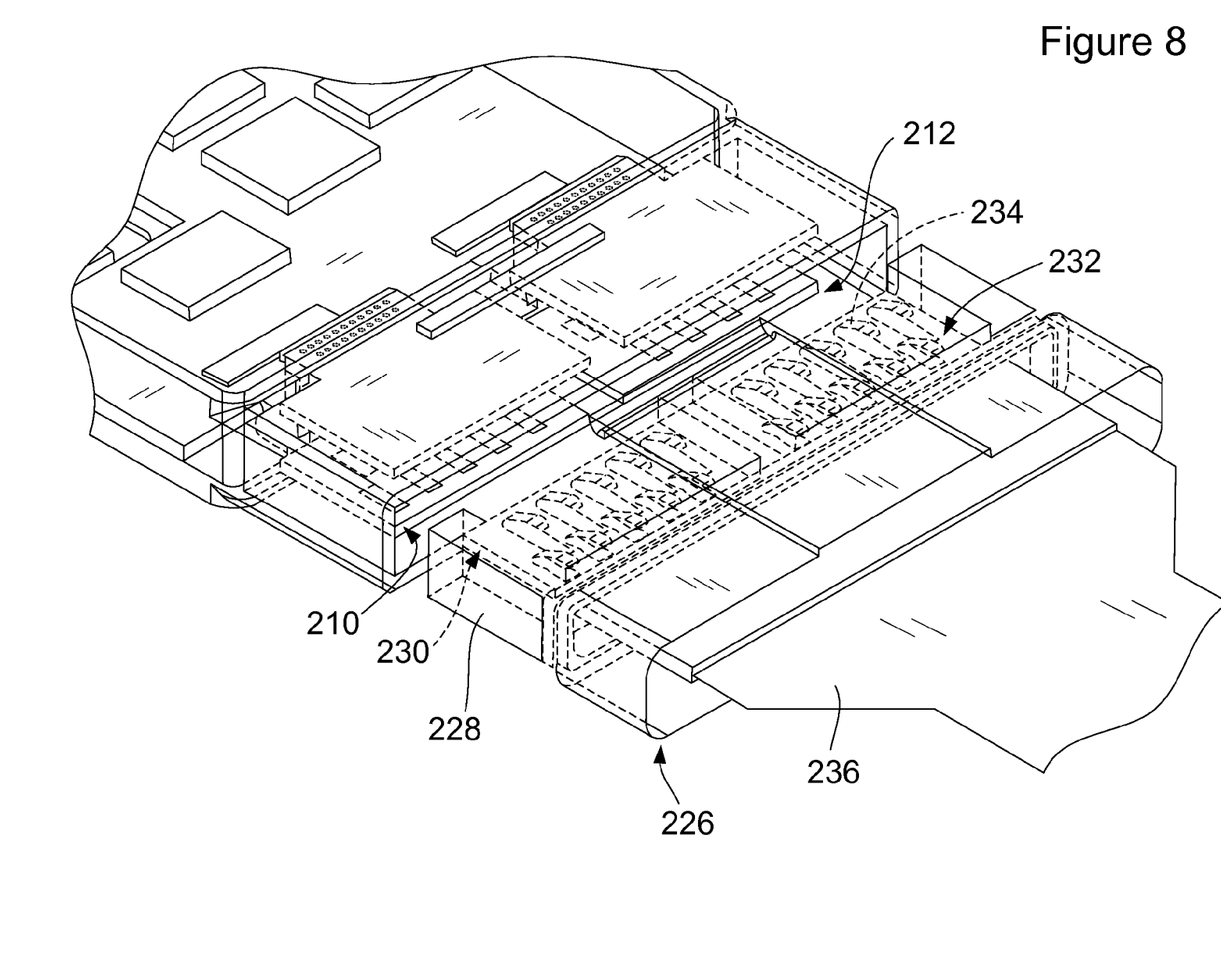
FIG. 8 is a perspective view of one of the male connector components about to be inserted into one of the connection interfaces.

As shown in FIG. 8, the connector components 210 and 212 may be secured to a mating connector 226 having a molding 228 which supports a pair of male connector components 230 and 232. The male connector components 230 and 232 each have a plurality of microsprings 234 made of an electrically conductive, biocompatible material secured thereto. The microsprings 234 in this example have a generally V-shape and are oriented sideways to facilitate sliding insertion into the connection interface 206. This also facilitates sliding engagement with the bond pads 222 on the opposing pair of connector components 210, and the bond pads 224 on the opposing pair of connector components 212. The microsprings 234 are electrically coupled to conductive traces carried in a cable portion 236 associated with the connector 226. As with the electrically conductive biasing elements 24 shown in FIG. 1, the microsprings could assume any suitable shape such as a C-shape, a leaf spring shape, etc. The important characteristic is that the microsprings 234 have at least a small degree of resiliency or compressibility to maintain a slight pressure on the bond pads 222 or 224 with which they are in physical contact.

Figure 9:
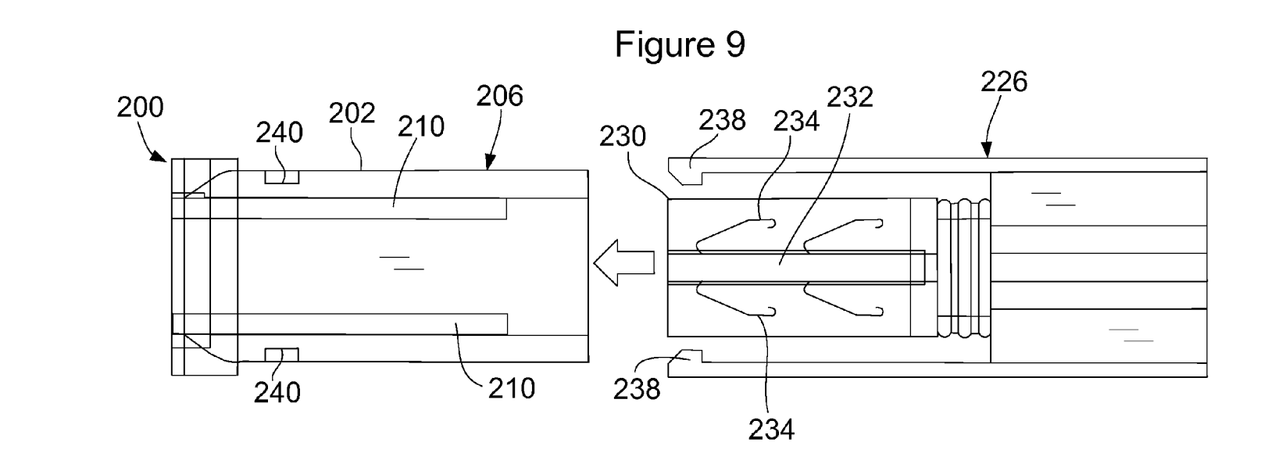
FIG. 9 is a side view showing the male connector component of FIG. 8 about to be inserted into the connection interface portion of the housing of FIG. 8.
Figure 10:
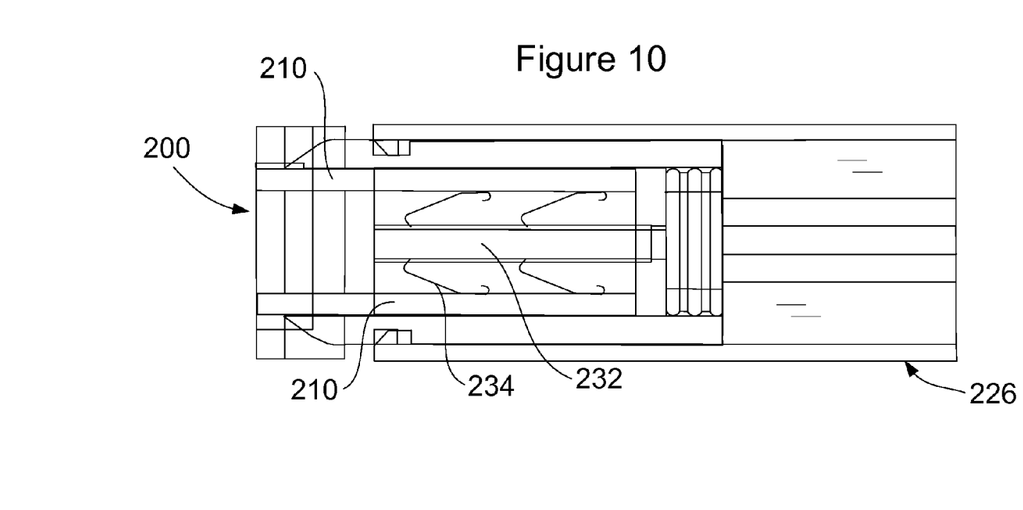
FIG. 10 is a side view of the two connector components of FIG. 9 assembled together.

FIGS. 9 and 10 illustrate the connection of the mating connector 226 to the housing 202. The connector 226 may have one or more flexible latching arms 238 which engage in recesses 240 to hold the housing 202 and the connector 226 together as the connector 226 is slidably inserted into the connection interface 206. Once fully engaged, the microsprings 234 contact the bond pads 222 and 224 of the connector components 210 and 212, respectively. A separate cable (not shown) having its own connector may be secured to the connector component 208 of FIG. 1 in the same manner.

In another embodiment, the housing 202 may be used as an "extension" which functions simply to interface two, three or more separate electrical cables with one another as needed. In such an embodiment, the circuit board 213 would be configured with conductive traces to make the desired electrical connections between the bond pads 220-224 of the connection interfaces 208-212.

The various embodiments thus enable a highly dense configuration of independent electrical connections to be made within a very limited area or volume. The various embodiments enable two or more independent electrical cables to be interfaced to a biocompatible implantable electrical connector system, and overcome the drawbacks of previous electrical connector systems which are limited in application because of their physical size and/or limited number of electrical connections that can be made. It is expected that the various embodiments described herein will find utility as implantable connector systems in various portions of human and/or animal anatomies where previous connector systems would have been impossible to implant because of the size of the connector system.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

What is claimed is:

1. A high density electrical connector system, the system comprising:
    a first connector component having a first substrate, the first substrate having a first plurality of electrical feedthroughs and at least a first plurality of electrically conductive bond pads in communication with the first plurality of electrical feedthroughs;
    a second connector component having a second substrate, the second substrate having a second plurality of electrical feedthroughs and at least a second plurality of electrically conductive bond pads in communication with the second plurality of electrical feedthroughs;
    a third plurality of electrically conductive bond pads formed on a surface of the first substrate opposite to that on which the first plurality of electrically conductive bond pads are present, the third plurality of electrically conductive bond pads being in communication with the first plurality of electrical feedthroughs and forming a plurality of direct paths through the first substrate;
    an electrical coupling subsystem disposed between the first and second connector components to make electrical contact between associated pairs of ones of the first plurality of electrically conductive bond pads and ones of the second plurality of electrically conductive bond pads;
    the electrical coupling subsystem including a plurality of independent electrically conductive miniature coil springs having dimensions in accordance with the first and second pluralities of bond pads, the plurality of independent electrically conductive miniature coil springs having parallel arranged end portions and being initially formed as a single cluster of coil spring portions with sacrificial material portions connecting the coil spring portions, and wherein removal of the sacrificial material portions results in formation of the independent electrically conductive miniature coil springs;
    the electrical coupling subsystem including a third plurality of electrically conductive miniature coil springs positioned to contact the third plurality of electrically conductive bond pads, for providing a corresponding plurality of independent electrical connections with the second plurality of electrically conductive bond pads; and
    a plurality of fasteners for clamping the first and second connector components in facing relationship such that said first and second pluralities of electrically conductive bond pads are in electrical contact with one another through the electrical coupling subsystem.

2. The system of claim 1, wherein the plurality of electrically conductive miniature coil springs are each attached to respective ones of the first or second pluralities of electrically conductive bond pads using at least one of laser welding, brazing, soldering, thermocompression, ultrasonic bonding or conductive epoxy.

3. The system of claim 1, further comprising a sealing ring interposed between the first and second substrates to circumscribe the electrically conductive miniature coil springs and seal the electrically conductive miniature coil springs from an ambient atmosphere.

4. The system of claim 3, wherein the sealing ring comprises a silicone sealing ring.

5. The system of claim 1, wherein:
    the sacrificial material portions are at least substantially removed after the single cluster of coil spring portions is secured to its associated one of the first or second substrates.

6. The system of claim 1, wherein at least one of the first and second substrates includes an electronic subsystem supported on the substrate and in communication with the electrical feedthroughs associated with the at least one of the first and second substrates.

7. The system of claim 1, wherein at least one of:
    the electrically conductive miniature coil springs are substantially surrounded by an electrically non-conductive material; or
    the first and second connector components contain routed electrically conductive traces between opposing faces thereof, in order to customize a geometry and location of the first and second pluralities of the electrically conductive bond pads.

8. A high density electrical connector system, the system comprising:
    a housing;
    at least one access port formed in the housing;
    a first connector component secured in the access port, the first connector component having a first substrate, the first substrate having a plurality of electrical feedthroughs and at least a first plurality of electrically conductive bond pads in communication with the plurality of electrical feedthroughs;
    a second connector component having a second substrate, the second substrate having dimensions enabling it to be inserted into the at least one access port; and
    the second substrate of the second connector component further including an electrical coupling subsystem including a plurality of electrically conductive, V-shaped microsprings, each of the microsprings having an apex and being arranged parallel to an axis of movement, and shaped to enable sliding insertion into the at least one access port along the axis of movement, and such that the apex of V-shaped microspring facilitates the sliding insertion, and further such that the microsprings make a plurality of independent electrical connections with the first plurality of electrically conductive bond pads, to thus form a plurality of independent electrical paths between the electrical coupling subsystem and the plurality of electrical feedthroughs.

9. The system of claim 8, wherein the electrical coupling subsystem of the second connector component is electrically coupled to a multi-conductor cable, and wherein the multi-conductor cable includes at least one of: a flat ribbon cable, a coiled cable assembly, or a straight bundled cable.

10. The system of claim 8, wherein an additional first connector component is secured in the access port in opposing, spaced apart relationship to the first connector component, with a spacing sufficient to receive a portion of the second connector component therebetween.

11. The system of claim 8, wherein the housing includes a circuit board in electrical communication with the connector component.

12. The system of claim 8, wherein the housing is hermetically sealed.

13. A method of forming a high density electrical connector system, the method comprising:
- forming a first connector component having a first substrate;
- forming a first plurality of electrical feedthroughs in the first substrate;
- forming a first plurality of electrically conductive bond pads on a surface of the first substrate, which are each in communication with respective ones of the first plurality of electrical feedthroughs;
- forming a second connector component having a second substrate;
- forming a second plurality of electrical feedthroughs in the second substrate;
- forming at least a second plurality of electrically conductive bond pads on the second substrate, which are each in communication with respective ones of the second plurality of electrical feedthroughs;
- forming a third plurality of electrically conductive bond pads on a surface of the first substrate opposite to that on which the first plurality of electrically conductive bond pads are present, the third plurality of electrically conductive bond pads being in communication with the first plurality of electrical feedthroughs and forming a plurality of direct paths through the first substrate;
- placing an electrical coupling subsystem including a plurality of independent, electrically conductive, miniature coil springs held together by sacrificial material portions as a single unit, between the first and second connector components to make electrical contact between associated pairs of ones of the first plurality of electrically conductive bond pads and ones of the second plurality of electrically conductive bond pads;
- separating the miniature coil springs into independent components by removing the sacrificial material portions;
- using a third plurality of electrically conductive miniature coil springs positioned to contact the third plurality of electrically conductive bond pads, for providing a corresponding plurality of independent electrically connections with the second plurality of electrically conductive bond pads; and
- using a plurality of fasteners for clamping the first and second connector components in facing relationship such that said first and second pluralities of electrically conductive bond pads are in electrical communication with one another through the electrical coupling subsystem.

\* \* \* \* \*